(12) United States Patent
Oravecz

(10) Patent No.: US 7,825,150 B2
(45) Date of Patent: Nov. 2, 2010

(54) COMPOSITIONS AND METHODS FOR TREATING IMMUNOLOGICAL AND INFLAMMATORY DISEASES AND DISORDERS

(75) Inventor: Tamas Oravecz, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 37 days.

(21) Appl. No.: 12/204,918

(22) Filed: Sep. 5, 2008

(65) Prior Publication Data

US 2009/0068180 A1   Mar. 12, 2009

Related U.S. Application Data

(60) Provisional application No. 60/970,416, filed on Sep. 6, 2007.

(51) Int. Cl.
| | |
|---|---|
| A01N 43/50 | (2006.01) |
| A61K 31/415 | (2006.01) |
| C07D 233/61 | (2006.01) |
| C07D 233/66 | (2006.01) |
| C07D 233/90 | (2006.01) |

(52) U.S. Cl. ............... 514/400; 548/335.5; 548/336.1; 548/337.1

(58) Field of Classification Search .......... 514/400; 548/335.5, 336.1, 337.1
See application file for complete search history.

(56) References Cited

U.S. PATENT DOCUMENTS

| | | | |
|---|---|---|---|
| 3,968,120 | A | 7/1976 | Regel |
| 4,567,194 | A | 1/1986 | Kroeplien |
| 4,614,662 | A | 9/1986 | Ramaswamy |
| 5,519,040 | A | 5/1996 | Chow |
| 5,561,134 | A | 10/1996 | Spada |
| 5,668,161 | A | 9/1997 | Talley |
| 5,716,929 | A | 2/1998 | Bemis |
| 5,843,971 | A | 12/1998 | Boar |
| 6,100,264 | A | 8/2000 | Aloup |
| 6,147,097 | A | 11/2000 | Sugimoto |
| 6,180,650 | B1 | 1/2001 | Frenette |
| 6,420,522 | B1 | 7/2002 | Bemis |
| 6,518,259 | B1 | 2/2003 | Holoshitz |
| 6,624,188 | B1 | 9/2003 | Chandraratna |
| 6,692,960 | B2 | 2/2004 | Bennett |
| 6,720,320 | B2 | 4/2004 | Nishiyama |
| 6,743,919 | B2 | 6/2004 | Koya |
| 6,997,961 | B2 | 2/2006 | Chassot |
| 7,041,291 | B2 | 5/2006 | Saba |
| 7,169,390 | B2 | 1/2007 | Sabbadini |
| 7,265,137 | B2 | 9/2007 | Sakuma |
| 7,649,098 | B2 | 1/2010 | Augeri |
| 2004/0039202 | A1 | 2/2004 | Sauter |
| 2005/0221346 | A1 | 10/2005 | Saba |
| 2005/0250794 | A1 | 11/2005 | Napper |
| 2006/0019952 | A1 | 1/2006 | Distefano |
| 2007/0154428 | A1 | 7/2007 | Sato |
| 2007/0208063 | A1 * | 9/2007 | Augeri et al. ............... 514/341 |
| 2008/0262241 | A1 | 10/2008 | Wu |
| 2009/0298901 | A1 | 12/2009 | Wu |

FOREIGN PATENT DOCUMENTS

| | | |
|---|---|---|
| DE | 04205081 | 8/1993 |
| JP | 08151386 | 6/1996 |
| WO | WO 93/06118 | 4/1993 |
| WO | WO 93/14752 | 8/1993 |
| WO | WO 97/46543 | 12/1997 |
| WO | WO 01/89460 | 11/2001 |
| WO | WO 03/028637 | 4/2003 |
| WO | WO 2004/071509 | 8/2004 |
| WO | WO 2005/075468 | 8/2005 |
| WO | WO 2006/135862 | 12/2006 |

OTHER PUBLICATIONS

Nakajima, Modern Rheumatology, 2006, Springer Japan, vol. 16, pp. 269-275.*
Chaudhuri et. al., Journal of the Royal Society of Medicine, 2005, Royal Society of Medicine, vol. 98, pp. 303-306.*
Monien et. al., Expert Reviews in Neurotherapeutics, 2006, Expert Reviews Ltd, vol. 6(9), pp. 1293-1306.*
Artavanis-Tsakonas et. al., Clinical & Experimental Immunology, 2003, British Society of Immunology, vol. 133, pp. 145-152.*
Aboody et. al., PLOS ONE, 2006, Public Library of Science, vol. 1, issue 1, pp. 1-10.*
Choi et. al., The Lancet, 2002, Williams & Wilkins, vol. 359, pp. 1173-1177.*
Uetrecht, Toxicology, 1997, Elsevier Science, vol. 119, pp. 37-43.*
Debandt et. al., Clinical Rheumatology, 2003, International League of Associations for Rheumatology, vol. 22, pp. 56-61.*
Sicotte et. al., Neurology, 2001, AAN Enterprises, vol. 57, No. 10, pp. 1885-1888.*
U.S. Appl. No. 12/628,309, filed Dec. 1, 2009, Augeri.
Cliff and Pyne, *J. Org. Chem.*, 62: 1023-1032 (1997).
Cliff and Pyne, *Tett. Letters*, 36(33): 5969-5972 (1995).

(Continued)

*Primary Examiner*—Sreeni Padmanabhan
*Assistant Examiner*—Sarah Pihonak
(74) *Attorney, Agent, or Firm*—Max Bachrach

(57) ABSTRACT

Methods and compositions for treating immunological and inflammatory diseases and disorders are disclosed. Particular methods and compositions comprise the administration of an agent that inhibits S1P lyase activity and at least one additional immunosuppressive and/or anti-inflammatory agent.

13 Claims, 2 Drawing Sheets

OTHER PUBLICATIONS

Figure 1:
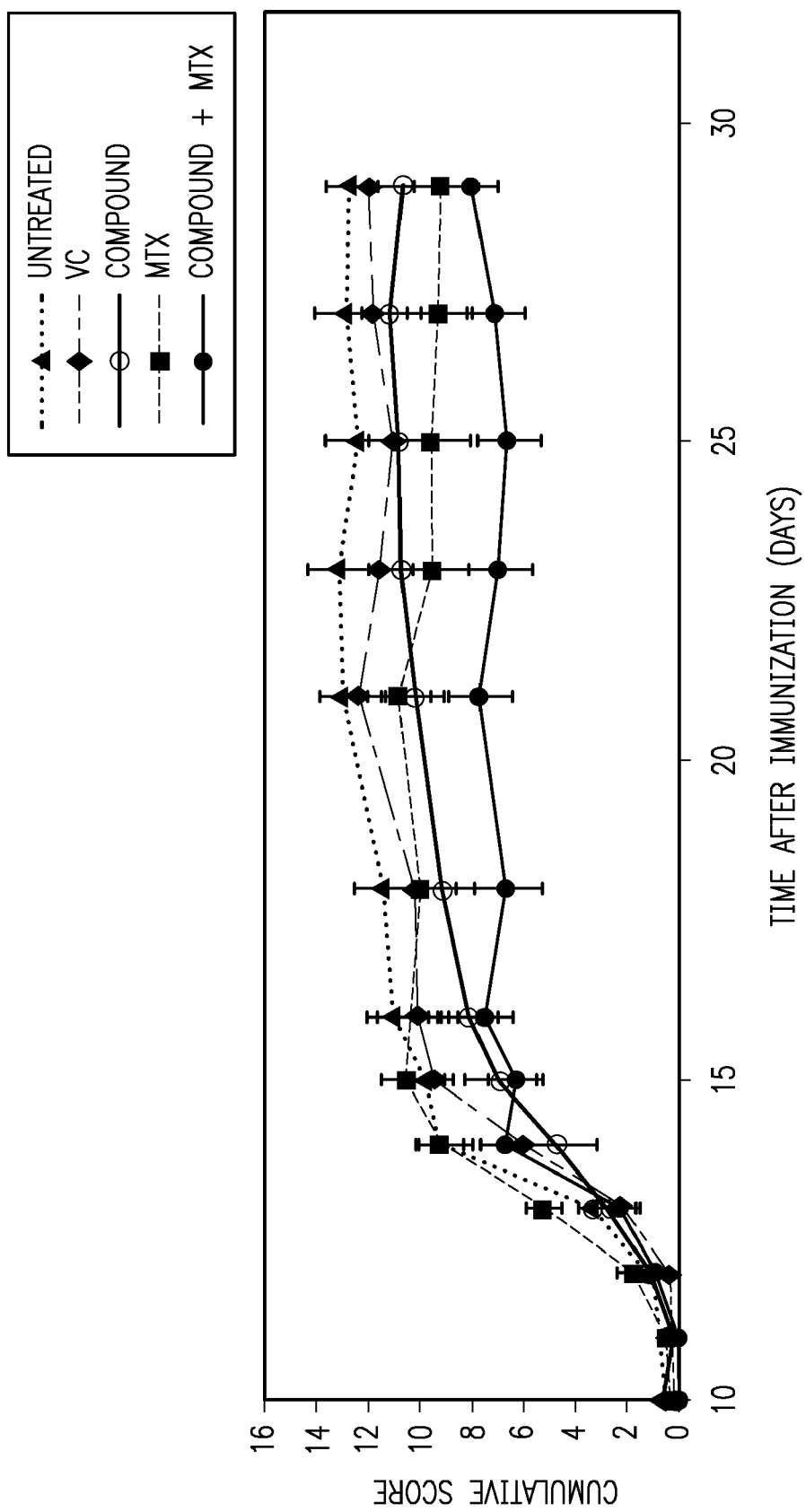

Gobin and Phillips, *Clin. Exp. Immunol.*, 85(2): 335-40 (1991).
Gugasyan et al., *Immunology Letters*, 58: 133-138 (1997).
Halweg and Buchi, *J. Org. Chem.*, 50(7): 1134-6 (1985).
HLA, *Science*, 309: 1682-3 (2005).
Houben et al., *Food Chem. Toxicol.*, 30(5): 427-30 (1992).
Houben et al., *Food Chem. Toxicol.*, 30(9): 749-57 (1992).
Jousserandot, Anne, et al., *Biochemistry* 37:17179-17191 (1998).
Pyne, Stephen G., *ACGC Chem. Res. Comm.* 11:108-112 (2000).
Pyne and Pyne, *Biochem. J.*, 349:385-402 (2000).
Pyne and Ung, *Synlett*, 280-282 (1998).
Schwab et al., *Science*, 309:1735-1739 (2005).
Sweeny et al., *J. Org. Chem.*, 50:1133-1134 (1985).
Ung and Pyne, *Tetrahedron: Asymmetry*, 9:1395-1407 (1998).
Ung and Pyne, *Tetrahedron Letters*, 37(34):6209-6212 (1996).
Search Report and Written Opinion for Corresponding International Application PCT/US2008/075320, dated Apr. 12, 2008.

\* cited by examiner

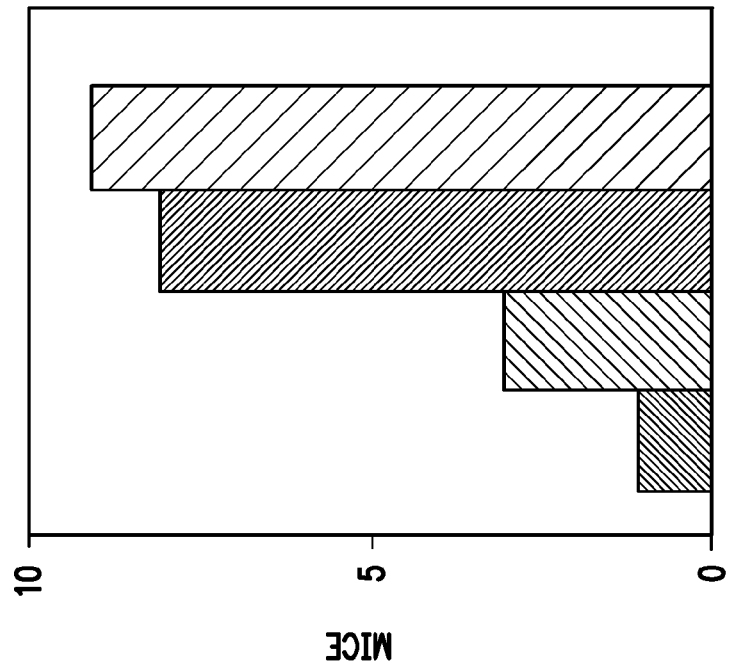
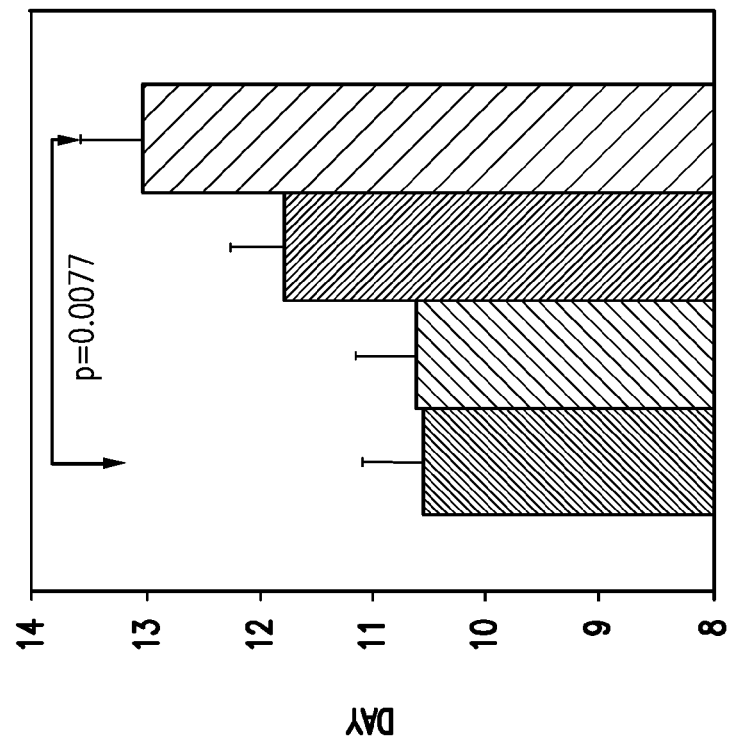
FIG. 2A
FIG. 2B

COMPOSITIONS AND METHODS FOR TREATING IMMUNOLOGICAL AND INFLAMMATORY DISEASES AND DISORDERS

This application claims priority to U.S. provisional application No. 60/970,416, filed Sep. 6, 2007, the entirety of which is incorporated herein by reference.

1. FIELD OF THE INVENTION

Methods and compositions for treating immunological and inflammatory diseases and disorders are disclosed. Particular methods and compositions comprise the administration of an agent that inhibits S1P lyase activity and at least one additional immunosuppressive and/or anti-inflammatory agent.

2. BACKGROUND

Sphingosine-1-phosphate (S1P) is a bioactive molecule with potent effects on multiple organ systems. Saba, J. D. and Hla, T. *Circ. Res.* 94:724-734 (2004). Although some believe the compound is an intracellular secondary messenger, its mode of action is still a subject of debate. Id. Indeed, even its metabolism is poorly understood. Hla, T., *Science* 309:1682-3 (2005). Researchers currently believe that S1P is formed by the phosphorylation of sphingosine, and degraded by dephosphorylation or cleavage. Its cleavage into ethanolamine phosphate and a long-chain aldehyde is reportedly catalyzed by S1P lyase. Id.; Pyne & Pyne, *Biochem J.* 349: 385-402 (2000).

Sphingosine-1-phosphate lyase is a vitamin $B_6$-dependent enzyme localized in the membrane of the endoplasmic reticulum. Van Veldhoven and Mannaerts, *J. Biol. Chem.* 266: 12502-12507 (1991); Van Veldhoven and Mannaerts, *Adv. Lipid. Res.* 26:69 (1993). The polynucleotide and amino acid sequences of human S1P lyase and its gene products are described in PCT Patent Application No. WO 99/16888.

Recently, Schwab and coworkers concluded that a component of caramel color III, 2-acetyl-4-tetrahydroxybutylimidazole (THI), inhibits S1P lyase activity when administered to mice. Schwab, S. et al, *Science* 309:1735-1739 (2005). While others have postulated that THI exerts its effects by a different mechanism (see, e.g., Pyne, S. G., *ACGC Chem. Res. Comm.* 11:108-112 (2000)), it is clear that administration of the compound to rats and mice induces lymphopenia and causes the accumulation of mature T cells in the thymus. See, e.g., Schwab, supra; Pyne, S. G., *ACGC Chem. Res. Comm.* 11:108-112 (2000); Gugsyan, R., et al., *Immunology* 93(3): 398-404 (1998); Halweg, K. M. and Büchi, G., *J. Org. Chem.* 50:1134-1136 (1985); U.S. Pat. No. 4,567,194 to Kroeplien and Rosdorfer. Still, there are no known reports of THI having an immunological effect in animals other than mice and rats. Although U.S. Pat. No. 4,567,194 alleges that THI and some related compounds may be useful as immunosuppressive medicinal agents, studies of the compound in humans found no immunological effects. See Thuvander, A. and Oskarsson, A., *Fd. Chem. Toxic.* 32(1):7-13 (1994); Houben, G. F., et al., *Fd. Chem. Toxic.* 30(9):749-757 (1992).

3. SUMMARY OF THE INVENTION

This invention is directed, in part, methods of treating, managing or preventing an immunological or inflammatory disease or disorder, which comprise inhibiting S1P lyase activity in a patient in need thereof and administering to the patient an immunosuppressant and/or an anti-inflammatory agent.

Inhibition of S1P lyase activity can be achieved by administering to the patient a compound of formula I:

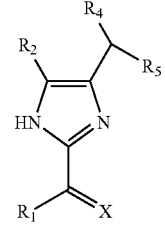

or a pharmaceutically acceptable salt thereof, the substituents of which are defined herein.

This invention also encompasses pharmaceutical compositions comprising compounds of formula I and one or more additional active agents.

4. BRIEF DESCRIPTION OF THE FIGURES

Certain aspects of this invention can be understood with reference to the attached figures.

FIG. 1 shows the effects of methotrexate ("MTX"), a S1P lyase inhibitor ("Compound"), and a combination of the two on collagen-induced arthritis in mice. These effects are compared to untreated mice, and mice administered a vehicle control ("VC").

FIG. 2 shows the effect of Compound administered alone and in combination with cyclosporin A ("CsA") in a transplantation model. FIG. 2A shows effect of vehicle, CsA alone, Compound alone, and the combination of the two on the day when the graft was rejected. FIG. 2B shows the effect of vehicle, CsA alone, Compound alone, and the combination of the two on the number of mice with greater than 10 days graft survival.

5. DETAILED DESCRIPTION

This invention results, in part, from discoveries relating to compounds that are believed to inhibit S1P lyase in vivo.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "circulating lymphocyte reduction agent" means a compound that has a CLRF of greater than about 20 percent.

Unless otherwise indicated, the term "circulating lymphocyte reduction factor" or "CLRF" means the decrease in the number of circulating lymphocytes in mice caused by oral administration of a single dose of a compound at 100 mg/kg, as determined by the method described in the Examples, below.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "S1P level enhancing agent" means a compound that has a SLEF of at least about 10-fold.

Unless otherwise indicated, the term "S1P level enhancing factor" or "SLEF" means the increase in S1P in the spleens of mice caused by oral administration of a single dose of a compound at 100 mg/kg, as determined by the method described in the Examples, below.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkyl-NHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alkyl, aryl, or heteroaryl" has the same meaning as "optionally substituted alkyl, optionally substituted aryl, or optionally substituted heteroaryl."

Unless otherwise indicated, a structure or name of a compound or genus of compounds encompasses all forms of that compound or genus of compounds, and all compositions comprising that compound or genus of compounds.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

This invention relates to methods of using, and compositions comprising, a compound that decreases S1P lyase activity in vivo and at least one additional pharmacological agent that affects immune or inflammatory response.

5.2.1. S1P Lyase Inhibitors

This invention contemplates the use of S1P lyase inhibitors disclosed in U.S. patent application Ser. No. 11/698,253, filed Jan. 25, 2007. Particular compounds are of formula I:

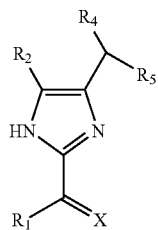

or are pharmaceutically acceptable salts thereof, wherein: X is O or $NR_3$; $R_1$ is $OR_{1A}$, NHOH, hydrogen, or optionally substituted alkyl, aryl, alkylaryl, arylalkyl, heteroalkyl, heterocycle, alkylheterocycle, or heterocyclealkyl; $R_2$ is $OR_{2A}$, $C(O)OR_{2A}$, hydrogen, halogen, nitrile, or optionally substituted alkyl, aryl, alkylaryl, arylalkyl, heteroalkyl, heterocycle, alkylheterocycle, or heterocyclealkyl; $R_3$ is $OR_{3A}$, $N(R_{3A})_2$, $NHC(O)R_{3A}$, $NHSO_2R_{3A}$, or hydrogen; $R_4$ is $OR_{4A}$, $OC(O)R_{4A}$, hydrogen, halogen, or optionally substituted alkyl, aryl, alkylaryl, arylalkyl, heteroalkyl, heterocycle, alkylheterocycle, or heterocyclealkyl; $R_5$ is $N(R_{5A})_2$, hydrogen, hydroxy, or optionally substituted alkyl, aryl, alkylaryl, arylalkyl, heteroalkyl, heterocycle, alkylheterocycle, or heterocyclealkyl; and each of $R_{1A}$, $R_{2A}$, $R_{3A}$, $R_{4A}$, and $R_{5A}$ is independently hydrogen or optionally substituted alkyl, aryl, alkylaryl, arylalkyl, heteroalkyl, heterocycle, alkylheterocycle, or heterocyclealkyl.

Particular compounds of formula I are such that if X is O; $R_1$ is alkyl of 1 to 4 carbons, phenyl, benzyl or phenylethyl; $R_2$ is hydrogen; and one of $R_4$ and $R_5$ is hydroxyl; the other of $R_4$ and $R_5$ is not alkyl of 1 to 6 carbons, hydroxyalkyl of 1 to 6 carbons, polyhydroxyalkyl of 1 to 6 carbons having up to one hydroxyl per carbon, polyacetylalkyl of 1 to 6 carbons having up to one acetyl per carbon, phenyl, benzyl or phenylethyl.

In particular embodiments, the compound is not 2-acetyl-4-tetrahydroxybutylimidazole, 1-(4-(1,1,2,2,4-pentahydroxybutyl)-1H-imidazol-2-yl)ethanone, 1-(2-acetyl-1H-imidazol-4-yl)butane-1,1,2,2-tetrayl tetraacetate, or 1-(2-acetyl-1H-imidazol-4-yl)butane-1,1,2,2,4-pentayl pentaacetate.

A particular embodiment encompasses compounds of formula II:

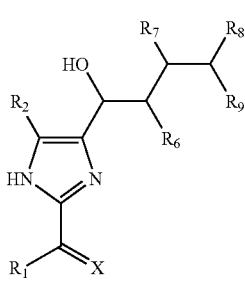

and pharmaceutically acceptable salts thereof, wherein: X is O or $NR_3$; $R_1$ is $OR_{1A}$, NHOH, hydrogen, or optionally substituted alkyl, aryl, alkylaryl, arylalkyl, heteroalkyl, heterocycle, alkylheterocycle, or heterocyclealkyl; $R_2$ is $OR_{2A}$, $C(O)OR_{2A}$, hydrogen, halogen, nitrile, or optionally substituted alkyl, aryl, alkylaryl, arylalkyl, heteroalkyl, heterocycle, alkylheterocycle, or heterocyclealkyl; $R_3$ is $OR_{3A}$, $N(R_{3A})_2$, $NHC(O)R_{3A}$, $NHSO_2R_{3A}$, or hydrogen; $R_6$ is $OR_{6A}$, $OC(O)R_{6A}$, $N(R_{6B})_2$, $NHC(O)R_{6B}$, hydrogen, or halogen; $R_7$ is $OR_{7A}$, $OC(O)R_{7A}$, $N(R_{7B})_2$, $NHC(O)R_{7B}$, hydrogen, or halogen; $R_8$ is $OR_{8A}$, $OC(O)R_{8A}$, $N(R_{8B})_2$, $NHC(O)R_{8B}$, hydrogen, or halogen; $R_9$ is $CH_2OR_{9A}$, $CH_2OC(O)R_{9A}$, $N(R_{9B})_2$, $NHC(O)R_{9B}$, hydrogen, or halogen; each of $R_{1A}$, $R_{2A}$, $R_{3A}$, $R_{6A}$, $R_{7A}$, $R_{8A}$ and $R_{9A}$ is independently hydrogen or optionally substituted alkyl, aryl, alkylaryl, arylalkyl, heteroalkyl, heterocycle, alkylheterocycle, or heterocyclealkyl; and each of $R_{6B}$, $R_{7B}$, $R_{8B}$ and $R_{9B}$ is independently hydrogen or alkyl optionally substituted with one or more hydroxy or halogen groups;

Particular compounds of formula II are such that: 1) if X is O, $R_1$ is alkyl of 1 to 4 carbons, phenyl, benzyl or phenylethyl, and $R_2$ is hydrogen, at least two of $R_6$, $R_7$, $R_8$ and $R_9$ are not hydroxyl or acetate; 2) if X is O, $R_1$ is methyl, $R_2$ is hydrogen, $R_6$ and $R_7$ are both hydroxyl, and one of $R_8$ and $R_9$ is hydrogen, the other is not $NHC(O)R_{9B}$; 3) if X is O, $R_1$ is $OR_{1A}$, $R_{1A}$ is hydrogen or lower alkyl, and $R_2$ is hydrogen, at least one, but not all, of $R_6$, $R_7$, $R_8$ and $R_9$ is hydroxyl or acetate.

Particular compounds of the invention are of formula II(a):

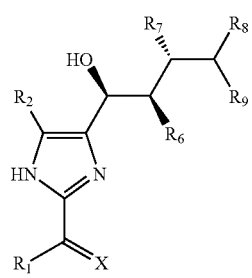

Others are of formula III:

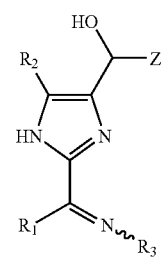

wherein: Z is optionally substituted alkyl; $R_1$ is $OR_{1A}$, NHOH, hydrogen, or optionally substituted alkyl, aryl, alkylaryl, arylalkyl, heteroalkyl, heterocycle, alkylheterocycle, or heterocyclealkyl; $R_2$ is $OR_{2A}$, $C(O)OR_{2A}$, hydrogen, halogen, nitrile, or optionally substituted alkyl, aryl, alkylaryl, arylalkyl, heteroalkyl, heterocycle, alkylheterocycle, or heterocyclealkyl; $R_3$ is $OR_{3A}$, $N(R_{3A})_2$, $NHC(O)R_{3A}$, $NHSO_2R_{3A}$, or hydrogen; and each of $R_{1A}$, $R_{2A}$, and $R_{3A}$ is independently hydrogen or optionally substituted alkyl, aryl, alkylaryl, arylalkyl, heteroalkyl, heterocycle, alkylheterocycle, or heterocyclealkyl. Particular compounds are of the formula:

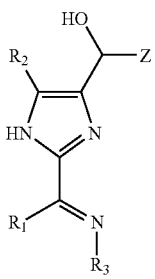

Another embodiment of the invention encompasses compounds of formula IV:

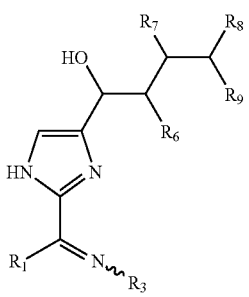

IV and pharmaceutically acceptable salts thereof, wherein: $R_1$ is $OR_{1A}$, NHOH, hydrogen, or optionally substituted alkyl, aryl, alkylaryl, arylalkyl, heteroalkyl, heterocycle, alkylheterocycle, or heterocyclealkyl; $R_3$ is $OR_{3A}$, $N(R_{3A})_2$, NHC(O)$R_{3A}$, $NHSO_2R_{3A}$, or hydrogen; $R_6$ is $OR_{6A}$, OC(O)$R_{6A}$, $N(R_{6B})_2$, NHC(O)$R_{6B}$, hydrogen, or halogen; $R_7$ is $OR_{7A}$, OC(O)$R_{7A}$, $N(R_{7B})_2$, NHC(O)$R_{7B}$, hydrogen, or halogen; $R_8$ is $OR_{8A}$, OC(O)$R_{8A}$, $N(R_{8B})_2$, NHC(O)$R_{8B}$, hydrogen, or halogen; $R_9$ is $CH_2OR_{9A}$, $CH_2OC(O)R_{9A}$, $N(R_{9B})_2$, NHC(O)$R_{9B}$, hydrogen, or halogen; and each of $R_{1A}$, $R_{3A}$, $R_{6A}$, $R_{7A}$, $R_{8A}$ and $R_{9A}$ is independently hydrogen or optionally substituted alkyl, aryl, alkylaryl, arylalkyl, heteroalkyl, heterocycle, alkylheterocycle, or heterocyclealkyl.

Particular compounds are of formula IV(a):

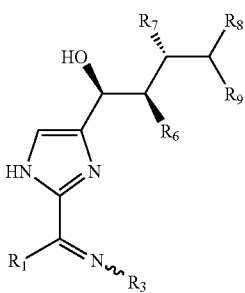

IV(a)

Others are of the formula:

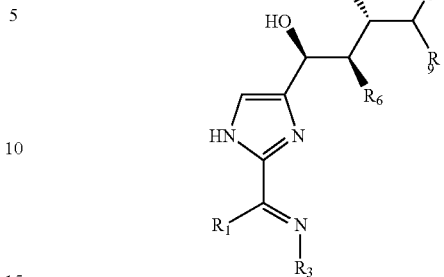

With regard to each of the formulae shown above that contain the moieties described below, certain embodiments of the invention are such that:

In some, X is O. In others, X is $NR_3$.

In some, $R_1$ is hydrogen. In others, $R_1$ is optionally substituted lower alkyl. In others, $R_1$ is NHOH. In others, $R_1$ is $OR_{1A}$ and $R_{1A}$ is, for example, hydrogen or optionally substituted lower alkyl.

In some, $R_2$ is hydrogen. In others, $R_2$ is not hydrogen. In others, $R_2$ is nitrile. In others, $R_2$ is optionally substituted lower alkyl. In others, $R_2$ is $OR_{2A}$. In others, $R_2$ is C(O)$OR_{2A}$. In some, $R_{2A}$ is hydrogen or optionally substituted lower alkyl.

In some, $R_3$ is $OR_{3A}$. In others, $R_3$ is $N(R_{3A})_2$ or NHC(O)$R_{3A}$. In others, $R_3$ is $NHSO_2R_{3A}$. In some, $R_{3A}$ is hydrogen or optionally substituted lower alkyl. In others, $R_{3A}$ is optionally substituted aryl or heterocycle.

In some, $R_4$ is $OR_{4A}$. In others, $R_4$ is halogen.

In some, $R_5$ is $N(R_{5A})_2$. In others, $R_5$ is hydrogen. In others, $R_5$ is hydroxyl. In others, $R_5$ is heteroalkyl (e.g., alkoxy). In others, $R_5$ is optionally substituted alkyl. In others, $R_5$ is optionally substituted aryl.

In some, one or more of $R_6$, $R_7$, $R_8$, and $R_9$ is hydroxy or halogen. In some, all of $R_6$, $R_7$, $R_8$, and $R_9$ are hydroxyl or acetate.

In some, Z is alkyl optionally substituted with one or more hydroxyl, acetate or halogen moieties.

Compounds of the invention (i.e., compounds disclosed herein) may contain one or more stereocenters, and can exist as racemic mixtures of enantiomers or mixtures of diastereomers. This invention encompasses stereomerically pure forms of such compounds, as well as mixtures of those forms. Stereoisomers may be asymmetrically synthesized or resolved using standard techniques such as chiral columns or chiral resolving agents. See, e.g., Jacques, J., et al, *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972).

This invention further encompasses stereoisomeric mixtures of compounds disclosed herein. It also encompasses configurational isomers of compounds disclosed herein, either in admixture or in pure or substantially pure form, such as cis (Z) and trans (E) alkene isomers and syn and anti oxime isomers.

Certain compounds are circulating lymphocyte reduction agents. Particular compounds inhibit the amount of circulating lymphocytes, as determined using the method described in the Examples, by greater than about 20, 50, 75, 100, 150 or 200 percent.

Certain compounds inhibit S1P lyase directly or indirectly in vivo, and are S1P level enhancing agents. Particular compounds increase the amount of S1P, as determined using the method described below in the Examples, by greater than about 10, 15, 20, 25, or 30-fold.

Compounds of formula I can be prepared by methods known in the art (e.g., by varying and adding to the approaches described in Pyne, S. G., *ACGC Chem. Res. Comm.* 11: 108-112 (2000); Halweg, K. M. and Büchi, G., *J. Org. Chem.* 50:1134-1136 (1985)), and by approaches described herein.

5.2.2. Immunosuppressive and Anti-Inflammatory Agents

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclomethasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

5.3. Methods of Use

This invention encompasses a method of treating, managing or preventing an immunological or inflammatory disease or disorder in a patient (e.g., a human), which comprises inhibiting S1P lyase activity in the patient and administering to the patient an immunosuppressive and/or anti-inflammatory drug that acts by a different mechanism.

Also encompassed by the invention is a method of reducing the dose of an immunosuppressive and/or anti-inflammatory drug necessary to treat, manage or prevent an immunological or inflammatory disease or disorder, which comprises adjunctively administering to the patient a compound that inhibits S1P lyase activity. This method allows one to reduce toxicities associated with many immunosuppressive and anti-inflammatory drugs while maintaining their efficacy.

Examples of immunological and inflammatory diseases and disorder include Addison's Disease, anti-phospholipid syndrome, asthma, atopic dermatitis, autoimmune atrophic gastritis, achlorhydra autoimmune, Behcet's disease, Celiac Disease, chronic idiopathic urticaria, Chronic infantile neurological cutaneous and articular (CINCA) syndrome (also known as neonatal-onset multisystem inflammatory disease (NOMID)), chronic obstructive pulmonary disease (COPD), Crohn's Disease, Cushing's Syndrome, dermatomyositis, Goodpasture's Syndrome, graft-vs-host disease, Grave's Disease, Hashimoto's thyroiditis, idiopathic adrenal atrophy, idiopathic thrombocytopenia, Lambert-Eaton Syndrome, lupus erythematosus, multiple sclerosis, pemphigoid, pemphigus vulgaris, pernicious anemia, pollinosis, polyarteritis nodosa, primary biliary cirrhosis, primary sclerosing cholangitis, psoriasis, Raynauds, Reiter's Syndrome, relapsing polychondritis, rheumatoid arthritis, rhinitis, Schmidt's Syndrome, sepsis, Sjogren's Syndrome, sympathetic ophthalmia, Takayasu's Arteritis, temporal arteritis, thyrotoxicosis, transplant rejection (e.g., tissue transplantation, bone marrow transplantation), ulcerative colitis, uveitis, vasculitis and Wegener's granulomatosis.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In a particular embodiment, a compound of formula I is administered to a human patient in an amount of about 0.5, 1, 2.5 or 5 mpk.

5.4. Pharmaceutical Formulations

This invention encompasses pharmaceutical compositions comprising at least two active pharmacological ingredients. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed. (Mack Publishing, Easton Pa.: 1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18th ed. (Mack Publishing, Easton Pa.: 1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 18th ed. (Mack Publishing, Easton Pa.: 1990); and *Introduction to Pharmaceutical Dosage Forms*, 4th ed. (Lea & Febiger, Philadelphia: 1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different forms of the active ingredients can be used to further adjust the properties of the resulting composition.

6. EXAMPLES

Aspects of this invention can be understood from the following examples, which do not limit its scope.

6.1. Synthesis of (E/Z)-1-(4-((1R,2S,3R)-1,2,3,4-tetrahydroxybutyl)-1H-imidazol-2-yl)-ethanone oxime

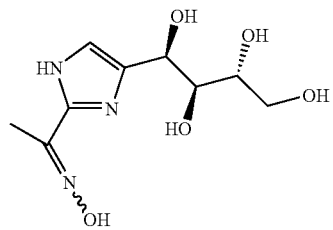

1-[4-((1R,2S,3R)-1,2,3,4-Tetrahydroxy-butyl)-1H-imidazol-2-yl]-ethanone (THI, prepared according to Halweg, K. M. and Büchi, G., *J. Org. Chem.* 50:1134-1136 (1985)) (350 mg, 1.52 mmol) was suspended in water (10 ml). Hydroxylamine hydrochloride (126.8 mg, 1.82 mmol, 1.2 eq.) and sodium acetate (247.3 mg, 3.04 mmol. 2 eq.) was added, and the suspension was stirred at 50° C. The reaction mixture turned clear after approximately 4 hours. Stirring was continued at 50° C. for 16 hours. LCMS analysis indicated the formation of the product and the absence of starting material. The reaction mixture was allowed to attain room temperature and passed through a fine porosity filter. This solution was used directly to purify the product by using preparative HPLC: Atlantis HILIC silica column 30×100 mm; 2%-21% water in acetonitrile over 6 minutes; 45 ml/min; with detection at 254 nm. The product fractions were collected and the acetonitrile was evaporated under reduced pressure. The aqueous solution was lyophilized to yield the product, a mixture of approximately 3:1 anti:syn isomers, as a white solid: 284 mg (77%).

LCMS: Sunfire C-18 column, 4.6×50 mm; 0-17% MeOH (0.1% TFA) in water (0.1% TFA) over 5 min; flow rate=3 ml/min; Detection 220 nm; Retention times: 0.56 min (syn isomer, 246.0 (M+1)) and 0.69 min (anti isomer, 246.0 (M+1)). $^1$H NMR (D$_2$O and DCl) δ 2.15 and 2.22 (singlets, 3H), 3.5-3.72 (m, 4H), 4.76 (br, OH protons and H$_2$O), 4.95 and 4.97 (singlets, 1H), 7.17 and 7.25 (singlets, 1H). $^{13}$C NMR (D$_2$O and DCl) δ 10.80, 16.76, 63.06, 64.59, 64.75, 70.86, 72.75, 72.85, 117.22, 117.64, 135.32, 138.39, 141.35, 144.12.

6.2. Synthesis of (E)-1-(4-((1R,2S,3R)-1,2,3,4-tetrahydroxybutyl)-1H-imidazol-2-yl)-ethanone Oxime

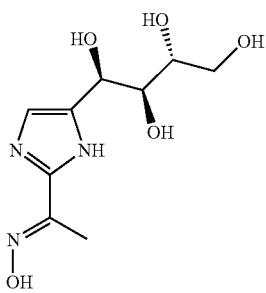

To a flask charged with THI (21.20 mmol, 4.88 g) was added water (25 ml) and 1N aqueous HCl (21.2 ml, 21.2 mmol). After all solids dissolved, a solution of trityl hydroxylamine (25.44 mmol, 7.00 g) in dioxane (55 ml) was added and the reaction was maintained at 50° C. for 4 h. At completion, the reaction was cooled room temperature and the solution was adjusted to pH=7 by addition of 1N aqueous NaOH. The neutralized solution was then concentrated to a plastic mass, which was purified by flash chromatography on silica gel [10% MeOH/1% NH$_4$OH (5% wt. solution in water) in DCM] to provide the trityl-ether as clear plastic. Treatment of the plastic mass with hexane and concentration provided a white foam, which could be dried under vacuum to a flaky solid (10.00 g, 97% yield).

To a vigorously stirred, room temperature solution of the trityl oxime-ether (4.8 g, 10 mmol) in dioxane (90 ml) was added a solution of HCl in dioxane (4M, 60 ml). After a few minutes, a white precipitant was observed, and stirring was continued for a total of 30 minutes, before filtering over a fritted glass filter and rinsing the cake with dioxane and ether. The cake was redissolved in water (200 ml), sonicated for 5 min, then cooled to 0° C., treated with celite (5 g), and filtered over a fritted glass filter. The aqueous solution was concentrated to dryness, then isolated from methanol (30 ml)/diethyl ether (60 ml) to provide the E-oxime as an analytically pure white powder (3.8 g, 80% yield).

6.3. Synthesis of (E/Z)-1-(4-((1R,2S,3R)-1,2,3,4-tetrahydroxybutyl)-1H-imidazol-2-yl)ethanone O-methyl Oxime

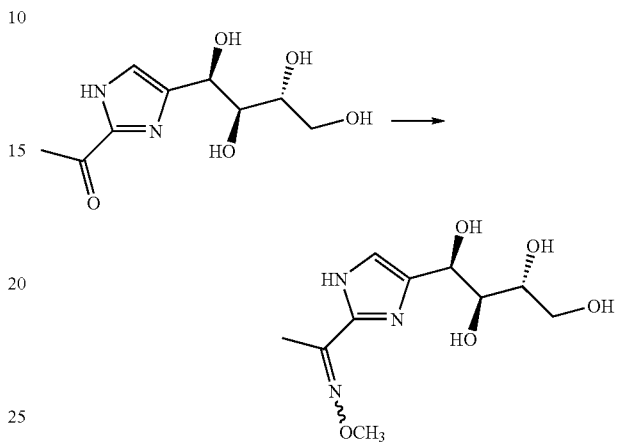

The captioned compound was prepared as described above in Example 6.1, by using methoxylamine hydrochloride in place of hydroxylamine hydrochloride, in 74% yield. The product was a white fluffy solid.

LCMS: Sunfire C-18 column, 4.6×50 mm; 0-17% MeOH (0.1% TFA) in water (0.1% TFA) over 5 min; flow rate=3 ml/min; Detection 220 nm; Retention times: 1.59 minutes (syn isomer, 260.1 (M+1)) and 1.73 min (anti isomer, 260.1 (M+1)). $^1$H NMR (D$_2$O) δ 2.18 and 2.22 (singlets, 3H), 3.54-3.60 (m, 1H), 3.66-3.79 (m, 3H), 3.94 and 3.95 (singlets, 3H), 4.76 (br, OH protons and H$_2$O), 4.93 and 4.97 (singlets, 1H), 7.17 and 7.25 (singlets, 1H). $^{13}$C NMR (D$_2$O) δ 11.55, 17.56, 62.32, 62.38, 62.99, 63.07, 67.09, 71.54, 73.86, 119.09, 138.64, 139.79, 142.95, 144.98, 148.97.

6.4. Synthesis of 1-(5-methyl-4-((1R,2S,3R)-1,2,3,4-tetrahydroxybutyl)-1H-imidazol-2-yl)ethanone

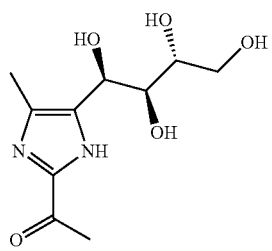

To a room temperature solution of 4-methyl imidazole (3.00 g, 36.54 mmol) in toluene (200 ml) was consecutively added triethylamine 5.6 ml, 40.20 mmol) and N,N-dimethylaminosulfamoyl chloride (3.9 ml, 36.54 mmol). The vessel was stored in a 5° C. refrigerator for 48 hours, then the solids were filtered off from the reaction and the liquor was concentrated to obtain a 2.5:1 mixture of regioisomers of 4-Methylimidazole-1-dimethylaminosulfonamide. The crude product was purified by flash chromatography over silica gel (80-

100% ethyl acetate:hexane eluent) to obtain the isomers in a 5.5:1 mixture (4.31 g, 62% yield): M+1=190.1

To a −78° C. solution of the 4-Methylimidazole-1-dimethylaminosulfonamide (1.99 g, 10.54 mmol) in tetrahydrofuran (70 ml) was added slowly a solution of n-BuLi in hexane (2.5M, 11.60 ml). After 40 minutes, N-methoxy-N-methylacetamide (1.30 g, 12.65 mmol) was added dropwise to the cooled solution. The reaction was allowed to warm to room temperature and maintained for 2 hours. At completion, the reaction was quenched by addition of saturated aqueous NH$_4$Cl (20 ml), then diluted with water (20 ml). The layers were separated, and the organic layer was washed with ethyl acetate (2×30 ml). The combined organics were washed with brine (20 ml), then dried over MgSO$_4$ and concentrated. The crude product was purified by flash chromatography over silica (60-80% ethyl acetate:hexane eluent) to provide 4-Methyl-2-acetylimidazole-1-dimethylaminosulfonamide as an oil (1.85 g, 76% yield): M+1=232.1.

To a solution of imidazole 4-Methyl-2-acetylimidazole-1-dimethylaminosulfonamide (1.65 g, 7.14 mmol) in dichloromethane (45 ml) was consecutively added triethylamine (1.00 ml, 14.28 mmol) and triisopropylsilyl trifluoromethanesulfonate (2.12 ml, 7.86 mmol). The reaction was maintained at room temperature for 20 hours, then quenched by the addition of saturated aqueous NaHCO$_3$ (20 ml). The mixture was diluted with water (20 ml) and the layers were separated. The aqueous layer was washed with dichloromethane (2×20 ml) and the combined organics were washed with brine solution (20 ml), then dried over MgSO$_4$ and concentrated. The resulting oil was purified by flash chromatography over silica gel (1-2% methanol:dichloromethane eluent) to provide 4-Methyl-2-(1-(triisopropylsilyloxy)vinyl)-1-dimethylaminosulfonamide as an orange oil (2.26 g, 83% yield): M+1=388.2.

To a −78° C. solution of 4-Methyl-2-(1-(triisopropylsilyloxy)vinyl)-1-dimethylaminosulfonamide (2.26 g, 5.84 mmol) in tetrahydrofuran (40 ml) was slowly added a hexane solution of n-BuLi (2.5M, 3.27 ml). After 30 minutes, a solution of (−)-2,3-O-isopropylidine-D-erythronolactone (1.66 g, 10.51 mmol) in tetrahydrofuran (10 ml) was added slowly to the −78° C. solution. The reaction was maintained at −78° C. for 2 hours, then allowed to warm to 0° C. before quenching the reaction by addition of saturated aqueous NH$_4$Cl (20 ml). The mixture was diluted with water (10 ml) and the layers were separated. The organics were washed with ethyl acetate (2×20 ml) and the combined organics were washed with brine (20 ml), then dried over MgSO$_4$ and concentrated. The crude product was purified on silica gel (30-50% ethyl acetate:hexane eluent) to provide 2.69 g (85% yield) of 5-((3aR,6aR)-4-hydroxy-2,2-dimethyltetrahydrofuro[3,4-d][1,3]dioxol-4-yl)-N,N,4-trimethyl-2-(1-(triisopropylsilyloxy)vinyl)-1H-imidazole-1-sulfonamide as a white foam: M+1=546.4.

To a 0° C. solution of 5-((3aR,6aR)-4-hydroxy-2,2-dimethyltetrahydrofuro[3,4-d][1,3]dioxol-4-yl)-N,N,4-trimethyl-2-(1-(triisopropylsilyloxy)vinyl)-1H-imidazole-1-sulfonamide (2.09 g, 3.83 mmol) in ethanol (70 ml) was added granular NaBH$_4$ (1.4 g, 38.32 mmol) in a few portions. After 2 hours, the reaction was warmed to room temperature for 30 minutes, then concentrated. The residue was redissolved in water (40 ml) and ethyl acetate (40 ml). The biphasic mixture was stirred vigorously for 10 minutes, then the layers were separated. The aqueous layer was washed with ethyl acetate (2×40 ml) and the combined organics were washed with brine (30 ml), then dried over MgSO$_4$ and concentrated. The crude foam was purified by flash chromatography over silica (5% methanol:dichloromethane eluent) to provide 5-((R)-hydroxy((4S,5R)-5-(hydroxymethyl)-2,2-dimethyl-1,3-dioxolan-4-yl)methyl)-N,N,4-trimethyl-2-(1-(triisopropylsilyloxy)vinyl)-1H-imidazole-1-sulfonamide (1.88 g, 90% yield) as a 3:1 mixture of inseparable diasteromers at the benzylic position: M+1=547.4.

Cesium fluoride (315 mg, 2.08 mmol) was added to a solution of 5-((R)-hydroxy((4S,5R)-5-(hydroxymethyl)-2,2-dimethyl-1,3-dioxolan-4-yl)methyl)-N,N,4-trimethyl-2-(1-(triisopropylsilyloxy)vinyl)-1H-imidazole-1-sulfonamide (567 mg, 1.04 mmol) in ethanol (10 ml) and warmed to 65° C. After 1 hour, the reaction was cooled to room temperature and treated with saturated aqueous NH$_4$Cl (1 ml), then concentrated. The crude product was purified by flash chromatography over silica gel (5% methanol:dichloromethane eluent) to provide 2-acetyl-5-((R)-hydroxy((4S,5R)-5-(hydroxymethyl)-2,2-dimethyl-1,3-dioxolan-4-yl)methyl)-N,N,4-trimethyl-1H-imidazole-1-sulfonamide (380 mg, 94% yield) as a white foam: M+1=392.1.

2-Acetyl-5-((R)-hydroxy((4S,5R)-5-(hydroxymethyl)-2,2-dimethyl-1,3-dioxolan-4-yl)methyl)-N,N,4-trimethyl-1H-imidazole-1-sulfonamide (380 mg, 0.97 mmol) was dissolved in acetone (6 ml) and consecutively treated with water (6 ml) and concentrated aqueous HCl (3 ml). The vessel was warmed to 40° C. for 45 minutes, then cooled to room temperature and concentrated. The crude material was purified by reverse phase preparative chromatography using a 150 mm×30 mm Zorbax C-6 column using unbuffered solvents by the following method: 1% acetonitrile:water isocratic run for 5 minutes (T$_R$=1.52 minutes). Following lyophilization, the captioned product was obtained as the dimethylaminosulfamic acid salt an amorphous solid: M+1=245.1; $^1$H NMR (400 MHz, CDCl$_3$) major δ 5.04 (d, 1H), 3.62 (comp. m, 2H), 3.42 (comp. m, 2H), 2.62 (s, 6H), 2.43 (s, 3H), 2.21 (s, 3H); minor δ 5.01 (d, 1H), 3.79 (comp. m, 2H), 3.55 (comp. m, 2H), 2.62 (s, 6H), 2.43 (s, 3H), 2.21 (s, 3H).

6.5. Synthesis of (1R,2S,3R)-1-(2-(1-hydrazonoethyl)-1H-imidazol-4-yl)butane-1,2,3,4-tetraol

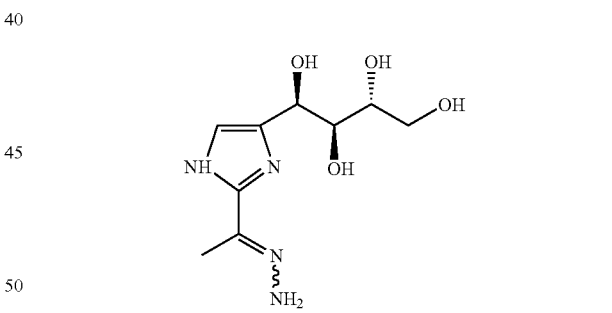

1-[4-((1R,2S,3R)-1,2,3,4-Tetrahydroxy-butyl)-1H-imidazol-2-yl]-ethanone (THI, prepared according to Halweg, K. M. and Büchi, G., J. Org. Chem. 50:1134-1136 (1985)) (148 mg, 0.64 mmol) was suspended in methanol (3 ml) and water (1 ml). Hydrazine hydrate (35 mg, 0.7 mmol, 1.2 eq.) and acetic acid (one drop) were added, and the suspension was stirred at 50° C. for 6 hours. LCMS analysis indicated the formation of the product and the absence of starting material. The reaction mixture was cooled to room temperature and diluted with tetrahydrofuran. The resulting white precipitate was collected and washed with tetrahydrofuran to yield the product, a mixture of approximately 3:1 E:Z isomers, as a white solid: 90 mg (58%).

LCMS: Zorbax C-8 column, 4.6×150 mm; 10-90% in water (10 mM ammonium acetate) over 6 min; flow rate=2 ml/min; Detection 220 nm; Retention times: 0.576 min (syn isomer, 245.0 (M+1)) and 1.08 min (anti isomer, 245.0 (M+1)). ¹H NMR (DMSO-d₆) δ 2.5 (singlet, 3H under DMSO), 3.4-3.7 (m, 4H), 4.3 (m, 2H), 4.6 (m, 2H), 4.8 (m, 1H), 4.9 and 5.0 (doublets, 1H), 7.04 and 7.21 (singlets, 1H).

6.6. Synthesis of N'-(1-(4-((1R,2S,3R)-1,2,3,4-tetrahydroxybutyl)-1H-imidazol-2-yl)ethylidene)acetohydrazide

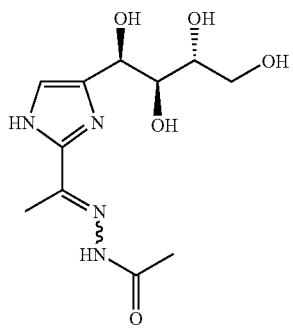

1-[4-((1R,2S,3R)-1,2,3,4-Tetrahydroxy-butyl)-1H-imidazol-2-yl]-ethanone (160 mg, 0.70 mmol) was suspended in methanol (3 ml) and water (1 ml). Acetic hydrazide (56 mg, 0.75 mmol, 1.2 eq.) and hydrochloric acid (one drop, 12 N) were added, and the suspension was stirred at 50° C. for 48 hours. LCMS analysis indicated the formation of the product and the absence of starting material. The reaction mixture was cooled to room temperature and diluted with tetrahydrofuran. The resulting white precipitate was collected and washed with tetrahydrofuran to yield the product, a mixture of approximately 3:1 E:Z isomers, as a white solid: 129 mg (65%).

LCMS: Sunfire C-18 column, 4.6×50 mm; 2-20% in water (10 mM ammonium acetate) over 2.5 min; flow rate=3.5 ml/min; Detection 220 nm; Retention time: 0.53 min (287.1 (M+1)). ¹H NMR (DMSO-d₆) δ 2.2 (singlets, 3H), 2.5 (singlets, 3H under DMSO), 3.4-3.7 (m, 4H), 4.3 (br, 2H), 4.6-5.0 (br, 4H), 7.0 (br, 1H), 10.30 and 10.37 (singlets, 1H).

6.7. Synthesis of (E)-4-methyl-N'-(1-(4-((1R,2S,3R)-1,2,3,4-tetrahydroxybutyl)-1H-imidazol-2-yl)ethylidene)benzenesulfonohydrazide

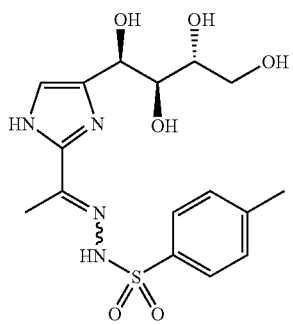

1-[4-((1R,2S,3R)-1,2,3,4-Tetrahydroxy-butyl)-1H-imidazol-2-yl]-ethanone (153 mg, 0.67 mmol) was suspended in methanol (3 ml) and water (1 ml). P-toluenesulfonyl hydrazide (140 mg, 0.75 mmol, 1.2 eq.) and hydrochloric acid (one drop, 12 N) were added, and the suspension was stirred at 50° C. for 24 hours. LCMS analysis indicated the formation of the product and the absence of starting material. The reaction mixture was cooled to room temperature and dry-loaded on silica gel. Flash chromatography on silica gel (10 g SiO₂, 4:1 ethyl acetate:methanol) to yield the product, a mixture of approximately 85:15 E:Z isomers, as a white solid: 142 mg (53%).

LCMS: Sunfire C-18 column, 4.6×50 mm; 10-90% in water (10 mM ammonium acetate) over 2.5 min; flow rate=3.5 ml/min; Detection 220 nm; Retention times: 0.50 min (399.2 (M+1)) and 0.66 min (399.3 (M+1)). ¹H NMR (Methanol-d₄) δ 2.2 (singlets, 3H), 2.41 and 2.45 (singlets, 3H), 3.6-3.85 (m, 4H), 4.99 and 5.05 (singlets, 1H), 7.09 (br s, 1H), 7.39 (d, 2H, j=8 Hz), 7.77 and 7.87 (d, 2H, j=8 Hz).

6.8. Synthesis of N'-(1-(4-((1R,2S,3R)-1,2,3,4-tetrahydroxybutyl)-1H-imidazol-2-yl)ethylidene)benzohydrazide

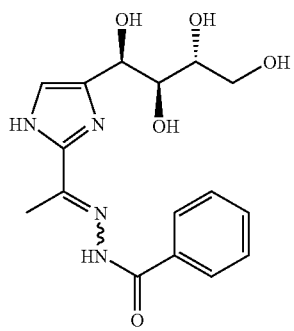

1-[4-((1R,2S,3R)-1,2,3,4-Tetrahydroxy-butyl)-1H-imidazol-2-yl]-ethanone (150 mg, 0.65 mmol) was suspended in methanol (3 ml) and water (1 ml). Benzoic acid hydrazide (102 mg, 0.75 mmol, 1.2 eq.) and hydrochloric acid (one drop, 12 N) were added, and the suspension was stirred at 50° C. for 18 hours. LCMS analysis indicated the formation of the product and the absence of starting material. The homogeneous reaction mixture was cooled to room temperature and concentrated in vacuo. C-18 Reverse-Phase SPE (10 g Alltech Hi-load C18, gradient from water to 20% methanol/water) to yield the product, a mixture of approximately 1:1 E:Z isomers, as a colorless solid: 193 mg (85%).

LCMS: Sunfire C-18 column, 4.6×50 mm; 10-90% in water (10 mM ammonium acetate) over 2.5 min; flow rate=3.5 ml/min; Detection 220 nm; Retention time: 0.49 min (349.2 (M+1)). ¹H NMR (Methanol-d₄) δ 2.2 (singlets, 3H), 2.42 and 2.45 (singlets, 3H), 3.6-3.85 (m, 4H), 5.11 and 5.14 (singlets, 1H), 7.30 (br s, 1H), 7.40-7.7 (m, 4H), 7.80 and 7.95 (m, 2H), 8.1 (br s, 1H).

6.9. Synthesis of (E)-ethyl 2-(1-(4-((1R,2S,3R)-1,2,3,4-tetrahydroxybutyl)-1H-imidazol-2-yl)ethylidene)hydrazinecarboxylate

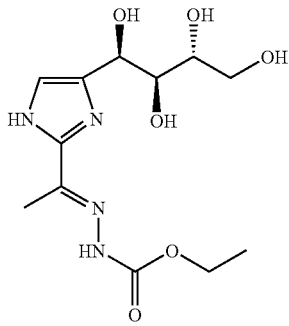

1-[4-((1R,2S,3R)-1,2,3,4-Tetrahydroxy-butyl)-1H-imidazol-2-yl]-ethanone (150 mg, 0.65 mmol) was suspended in methanol (3 ml) and water (1 ml). Ethyl carbazate (78 mg, 0.75 mmol, 1.2 eq.) and hydrochloric acid (one drop, 12 N) were added, and the suspension was stirred at 50° C. for 18 hours. LCMS analysis indicated the formation of the product and the absence of starting material. The reaction mixture was cooled to room temperature, concentrated in vacuo, and diluted with acetone. The resulting white precipitate was collected and washed with acetone to yield the product, one apparent isomer, as a white solid: 96 mg (47%).

LCMS: Sunfire C-18 column, 4.6×50 mm; 2-20% in water (10 mM ammonium acetate) over 2.5 min; flow rate=3.5 ml/min; Detection 220 nm; Retention time: 0.25 min (317.35 (M+1)). $^1$H NMR (Methanol-$d_4$) δ 1.36 (t, 3H, j=8 Hz), 2.28 (s, 3H), 2.42 and 2.45 (singlets, 3H), 3.60-3.85 (m, 4H), 4.34 (dd, 2H, j=8 Hz), 5.08 (s, 1H), 7.27 (s, 1H).

6.10. Synthesis of (E)-N'-(1-(4-((1R,2S,3R)-1,2,3,4-tetrahydroxybutyl)-1H-imidazol-2-yl)ethylidene)nicotinohydrazide

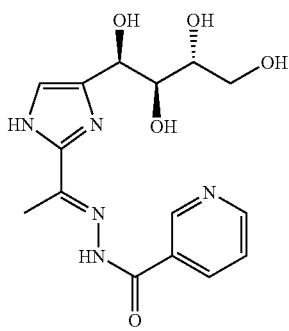

1-[4-((1R,2S,3R)-1,2,3,4-Tetrahydroxy-butyl)-1H-imidazol-2-yl]-ethanone (215 mg, 0.93 mmol) was suspended in methanol (3 ml) and water (1 ml). Nicotinic acid hydrazide (137 mg, 1.0 mmol, 1.1 eq.) and hydrochloric acid (one drop, 12 N) were added, and the suspension was stirred at 50° C. for 48 hours. LCMS analysis indicated the formation of the product and the absence of starting material. The reaction mixture was cooled to room temperature, and partially concentrated in vacuo. The resulting white precipitate was collected and washed with water to yield the product, one apparent isomer, as a white solid: 311 mg (95%).

LCMS: Sunfire C-18 column, 4.6×50 mm; 10-90% in water (10 mM ammonium acetate) over 2.5 min; flow rate=3.5 ml/min; Detection 220 nm; Retention time: 0.22 min (350.27 (M+1)). $^1$H NMR (DMSO-$d_6$) δ 2.37 (s, 3H), 3.60-3.85 (m, 4H), 4.40 (m, 2H), 4.71 (m, 1H), 5.01 (m, 2H), 5.16 (m, 1H), 7.25 (br, 1H), 7.64 (br, 1H). 8.35 (br, 1H). 8.80 (br, 1H). 9.14 (br, 1H).

6.11. Synthesis of 3-chloro-N'-(1-(4-((1R,2S,3R)-1,2,3,4-tetrahydroxybutyl)-1H-imidazol-2-yl)ethylidene)benzohydrazide

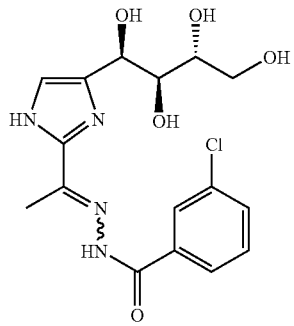

1-[4-((1R,2S,3R)-1,2,3,4-Tetrahydroxy-butyl)-1H-imidazol-2-yl]-ethanone (194 mg, 0.84 mmol) was suspended in ethanol (4 ml) and water (1 ml). 3-Chlorobenzoic acid hydrazide (170 mg, 1.0 mmol, 1.2 eq.) and hydrochloric acid (one drop, 12 N) were added, and the suspension was stirred at 50° C. for 48 hours. LCMS analysis indicated the formation of the product and the absence of starting material. The reaction mixture was cooled to room temperature, and partially concentrated in vacuo. The resulting white precipitate was collected and washed with ethanol to yield the product, as a ~3:1 E:Z mixture, as a white solid: 108 mg (33%).

LCMS: Sunfire C-18 column, 4.6×50 mm; 10-90% in water (10 mM ammonium acetate) over 2.5 min; flow rate=3.5 ml/min; Detection 220 nm; Retention time: 0.63 min (383.23 (M+1)). $^1$H NMR (Methanol-$d_4$) δ 2.44 (s, 3H), 3.60-3.90 (m, 4H), 5.12 (s, 1H), 7.29 (s, 1H), 7.65 (m, 2H), 8.04 (m, 2H).

6.12. Synthesis of (E)-4-fluoro-N'-(1-(4-((1R,2S,3R)-1,2,3,4-tetrahydroxybutyl)-1H-imidazol-2-yl)ethylidene)benzohydrazide

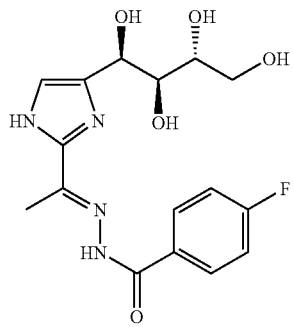

1-[4-((1R,2S,3R)-1,2,3,4-Tetrahydroxy-butyl)-1H-imidazol-2-yl]-ethanone (172 mg, 0.74 mmol) was suspended in ethanol (4 ml) and water (1 ml). 4-fluorobenzoic acid hydrazide (131 mg, 0.85 mmol, 1.1 eq.) and hydrochloric acid (one drop, 12 N) were added, and the suspension was stirred at 55° C. for 48 hours. LCMS analysis indicated the formation of the product and the absence of starting material. The reaction mixture was cooled to room temperature, and partially concentrated in vacuo. The resulting white precipitate was collected and washed with ethanol to yield the product, as one apparent isomer, as a white solid: 97 mg (35%).

LCMS: Sunfire C-18 column, 4.6×50 mm; 10-90% in water (10 mM ammonium acetate) over 2.5 min; flow rate=3.5 ml/min; Detection 220 nm; Retention time: 0.55 min (367.24 (M+1)). $^1$H NMR (Methanol-$d_4$, one drop DCl) δ 2.55 (s, 3H), 3.60-3.90 (m, 4H), 5.22 (s, 1H), 7.30 (m, 2H), 7.54 (s, 1H), 8.08 (m, 2H).

6.13. Synthesis of (E)-6-amino-N'-(1-(4-((1R,2S,3R)-1,2,3,4-tetrahydroxybutyl)-1H-imidazol-2-yl)ethylidene)nicotinohydrazide

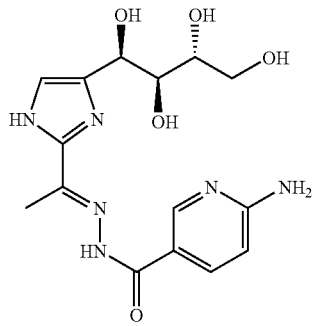

1-[4-((1R,2S,3R)-1,2,3,4-Tetrahydroxy-butyl)-1H-imidazol-2-yl]-ethanone (115 mg, 0.50 mmol) was suspended in ethanol (4 ml) and water (1 ml). Substituted hydrazide (91 mg, 0.6 mmol, 1.2 eq.) and hydrochloric acid (one drop, 12 N) were added, and the suspension was stirred at 55° C. for 48 hours. LCMS analysis indicated the formation of the product and the absence of starting material. The reaction mixture was cooled to room temperature, and partially concentrated in vacuo. The resulting white precipitate was collected and washed with ethanol to yield the product, as one apparent isomer, as a white solid: 136 mg (75%).

LCMS: Sunfire C-18 column, 4.6×50 mm; 10-90% in water (10 mM ammonium acetate) over 2.5 min; flow rate=3.5 ml/min; Detection 220 nm; Retention time: 0.15 min (365.32 (M+1)). $^1$H NMR (Methanol-$d_4$, one drop DCl) δ 2.58 (s, 3H), 3.60-3.90 (m, 4H), 5.22 (s, 1H), 7.17 (m, 1H), 7.54 (m, 1H), 8.44 (m, 1H), 8.68 (m, 1H).

6.14. Synthesis of (E)-N'-(1-(4-((1R,2S,3R)-1,2,3,4-tetrahydroxybutyl)-1H-imidazol-2-yl)ethylidene)isonicotinohydrazide

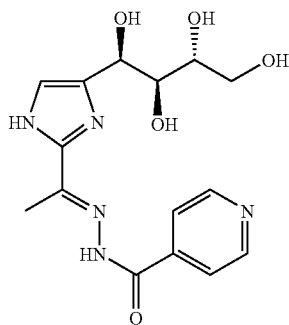

1-[4-((1R,2S,3R)-1,2,3,4-Tetrahydroxy-butyl)-1H-imidazol-2-yl]-ethanone (168 mg, 0.73 mmol) was suspended in ethanol (4 ml) and water (1 ml). Isonicotinic hydrazide (110 mg, 0.80 mmol, 1.1 eq.) and hydrochloric acid (one drop, 12 N) were added, and the suspension was stirred at 55° C. for 24 hours. LCMS analysis indicated the formation of the product and the absence of starting material. The reaction mixture was cooled to room temperature, and partially concentrated in vacuo. The resulting white precipitate was collected and washed with ethanol to yield the product, as one apparent isomer, as a white solid: 136 mg (75%).

LCMS: Sunfire C-18 column, 4.6×50 mm; 10-90% in water (10 mM Ammonium Acetate) over 2.5 min; flow rate=3.5 ml/min; Detection 220 nm; Retention time: 0.15 min (365.32 (M+1)). $^1$H NMR (Methanol-$d_4$, one drop DCl) δ 2.63 (s, 3H), 3.60-3.90 (m, 4H), 5.12 (s, 1H), 7.58 (s, 1H), 8.63 (d, 2H, j=8 Hz), 9.14 (d, 2H, j=8 Hz).

6.15. Synthesis of (E)-N'-(1-(4-((1R,2S,3R)-1,2,3,4-tetrahydroxybutyl)-1H-imidazol-2-yl)ethylidene)biphenyl-3-carbohydrazide

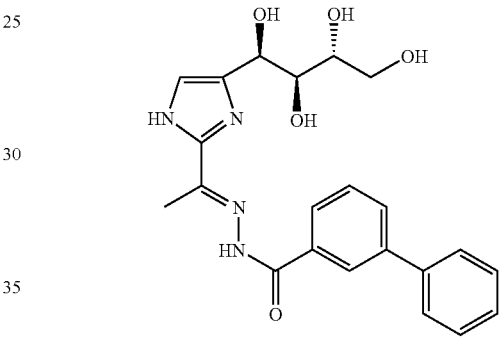

1-[4-((1R,2S,3R)-1,2,3,4-Tetrahydroxy-butyl)-1H-imidazol-2-yl]-ethanone (315 mg, 1.36 mmol) and biphenyl-3-carbohydrazide (360 mg, 1.81 mmol) were suspended in DMSO (2 ml). Concentrated hydrochloric acid (two drops) was added, and the suspension was stirred at 40° C. for 5 hours. LCMS analysis indicated the formation of the product and the absence of starting material. The reaction mixture was cooled to room temperature, diluted with methanol and purified by reverse phase HPLC (10 mM NH$_4$OAc/acetonitrile). Two fractions (E and Z isomers) of the desired mass were collected separately and lyophilized. Fraction one afforded a white solid, 95 mg (16%). Fraction two was a white solid, 82 mg (14%).

Fraction one: Analytical HPLC Zorbax C-8 column, 4.6×150 mm; Solvent A=10 mM ammonium acetate; Solvent B=MeCN; 5% B at 0 min, 5% B at 1 min, 90% B at 3 min, 4 min stop; flow rate=3 ml/min; Detection 220 nm; Retention time: 2.9 min (note: contains ~5% of the other isomer). M+H=425.28. $^1$H NMR (DMSO-d6 with 2 drops D$_2$O) δ 2.3 (singlet, 3H), 3.3-3.7 (m, 4H), 4.9 (m, 1H), 7.19 (s, 1H), 7.37 (m, 1H) 7.47 (m, 2H), 7.67 (m, 3H), 7.85-7.92 (m, 2H) and 8.15 (s, 1H). HSQC of the same sample correlated the proton signal at 2.3 (CH$_3$) with a carbon signal at 20 ppm.

Fraction two: Analytical HPLC Zorbax C-8 column, 4.6×150 mm; Solvent A=10 mM ammonium acetate; Solvent B=MeCN; 5% B at 0 min, 5% B at 1 min, 90% B at 3 min, 4 min stop; flow rate=3 ml/min; Detection 220 nm; Retention time: 2.963 min (note: contains ~6% of the other isomer). M+H=425.28. $^1$H NMR (DMSO-d$_6$ with 2 drops D$_2$O) δ 2.4

(singlet, 3H), 3.4-3.6 (m, 4H), 4.77 and 4.86 (broad singlets, combined=1H), 6.9 and 7.1 (broad singlets, combined=1H), 7.40 (m, 1H) 7.50 (m, 2H), 7.61 (m, 1H), 7.73 (m, 2H), 7.87 (m, 2H) and 8.10 (s, 1H). HSQC of the same sample correlated the proton signal at 2.4 ($CH_3$) with a carbon signal at 13 ppm.

6.16. Synthesis of N-hydroxy-4-((1R,2S,3R)-1,2,3,4-tetrahydroxybutyl)-1H-imidazole-2-carboxamide

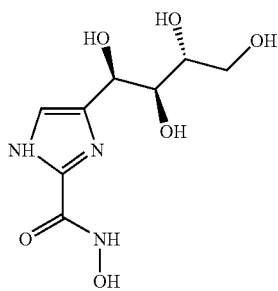

1-[4-((1R,2S,3R)-1,2,3,4-Tetrahydroxy-butyl)-1H-imidazol-2-yl]-ethanone (18 g, 78.3 mmol) was suspended in dichloroethane (160 ml) and 2,2-dimethoxy propane (160 ml). 4-toluenesulfonic acid (3 g) was added and the mixture stirred at 70° C. for 18 hours. The reaction was diluted with dichloromethane and washed with water, 5% bicarbonate, brine and then dry loaded onto $SiO_2$. Purification by flash chromatography (hexane/ethyl acetate) afforded 1-(4-((4S,4'R,5R)-2,2,2',2'-tetramethyl-4,4'-bi(1,3-dioxolan)-5-yl)-1H-imidazol-2-yl)ethanone as a colorless oil (18.8 g, 60.6 mmol, 77%; M+H calc: 311.4, obs: 311.3).

The product obtained above (20 g, 64.5 mmol) was dissolved in DMF. $K_2CO_3$ was added (12.5 g, 90.3 mmol) followed by benzyl bromide (10.7 ml, 90.3 mmol). The reaction was heated at 50° C. for 18 h. LC/MS analysis indicated starting material remained. An additional portion of benzyl bromide (5 ml, 42 mmol) was added and the temperature increased to 60° C. After 3 hours the reaction was quenched with cold water and extracted with ethyl acetate. The organic extracts were washed with water, then brine, dried over sodium sulfate, and loaded onto silica gel. Flash chromatography (20 to 40% ethyl acetate in hexane) afforded 1-(1-benzyl-4-((4S,4'R,5R)-2,2,2',2'-tetramethyl-4,4'-bi(1,3-dioxolan)-5-yl)-1H-imidazol-2-yl)ethanone (16.1 g, 62%).

The intermediate obtained (13 g, 32.5 mmol) was dissolved in dioxane (120 ml) and treated with NaOH (13.2 g) dissolved in commercial bleach (200 ml, 6% NaOCl). After 2 h of vigorous stirring, the reaction was extracted with ethyl acetate. Organic extracts were washed with brine then dried over celite. Filtration and evaporation afforded a solid that was further dried in vacuo to afford 1-benzyl-4-((4S,4'R,5R)-2,2,2',2'-tetramethyl-4,4'-bi(1,3-dioxolan)-5-yl)-1H-imidazole-2-carboxylic acid (13 g, quantitative yield, M+H calc: 403.2, obs: 403.2).

The product obtained above (600 mg, 1.49 mmol), O-tritylhydroxylamine (820 mg, 2.98 mmol), EDAC (430 mg, 2.24 mmol) and HOBt (305 mg, 2.24 mmol) were combined with DMF (8 ml) and triethylamine (622 µl, 4.47 mmol). The reaction was stirred at ambient temperature for 22 h, concentrated and then loaded onto silica using DCM/MeOH. Flash chromatography (MeOH/DCM) afforded 1-benzyl-4-((4S,4'R,5R)-2,2,2',2'-tetramethyl-4,4'-bi(1,3-dioxolan)-5-yl)-N-(trityloxy)-1H-imidazole-2-carboxamide (480 mg, 0.73 mmol, 49%, M+H calc: 660.3, obs: 660.4).

The product obtained above (480 mg, 0.73 mmol) was dissolved in ethanol (50 ml). $Pd(OH)_2$ (500 mg, 20% on carbon, wet) was added and the reaction stirred under $H_2$ (65 psi) for 18 h and filtered. Ethanol was removed in vacuo. The residue was dissolved in DCM and purified by flash chromatography (MeOH/DCM) to afford N-hydroxy-4-((4S,4'R,5R)-2,2,2',2'-tetramethyl-4,4'-bi(1,3-dioxolan)-5-yl)-1H-imidazole-2-carboxamide (150 mg, 0.46 mmol, 63%, M+H calc: 328.1, obs: 328.3).

The product obtained above (150 mg, 0.46 mmol) was dissolved in acetone (8 ml) and water (8 ml). The reaction was cooled to an internal temperature –15° C. using a dry ice/acetone bath. Concentrated HCl (3 ml) was added at a rate such that the internal temperature remained below –10° C. The cold bath was removed and the reaction stirred at ambient temperature for 3 hours, at 4° C. for 18 h and again at ambient temperature for 7 hours. After removal of the acetone and some water in vacuo, a precipitate formed. Dioxane (20 ml) was added followed by THF (10 ml). The solid was isolated by filtration, washed with THF/dioxane and dried in vacuo to afford N-hydroxy-4-((1R,2S,3R)-1,2,3,4-tetrahydroxybutyl)-1H-imidazole-2-carboxamide as the hydrochloride salt (98 mg, 0.40 mmol, 87%).

Mass spec.: M+H calc: 248.1, obs: 248.2. Analytical HPLC: Luna Phenyl-Hexyl, 5 um, 4.6×50 mm, isocratic 10 mM ammonium acetate with 1% acetonitrile, flow rate=3 ml/min, 220 nm detection, retention time=0.245 min. $^1$H NMR (DMSO-$d_6$) δ 3.37-3.64 (m, 4H), 4.96 (broad singlet, 1H), 7.47 (s, 1H), 11.9 (broad singlet, 1H).

6.17. Measuring Effects on Lymphocytes in Mice

Compounds were administered by oral gavage or in drinking water. For oral dosing experiments, compounds were resuspended from crystals at 10 mg/ml in vehicle (e.g., water). Mice (F1 hybrids of 129/B6 strain) were gavaged with a single 100 mg/kg dose of compound (equivalent to 100 mpk of the free base for each compound) or a vehicle-only control, and returned to their cages. Mice were anesthetized using isofluorane eighteen hours after dosing and tissues were collected for analysis as described below. For drinking water studies, compounds were dissolved at 50 mg/L in acidified water (pH=2.8) containing 10 g/L glucose. The mice were allowed free access to compound-containing water (or glucose solution as a control) for 72 hours. At the end of 72 hours, tissues were collected for analysis.

CBC measurements were obtained as follows. Mice were anesthetized with isofluorane and blood was collected from the retroorbital plexus into EDTA blood collection tubes (Capiject-MQK, Terumo Medical Corp., Elkton, Md.). Automated CBC analysis was performed using a Cell-Dyn 3500 (Abbott Diagnostics, Abbott Park, Ill.) or a HemaVet 850 (Drew Scientific, Inc., Oxford, Conn.) instrument.

Flow cytometry (FACS) measurements were obtained as follows. Twenty five µl whole blood was lysed by hyoptonic shock, washed once in 2 ml FACS wash buffer (FWB: PBS/0.1% BSA/0.1% $NaN_3$/2 mM EDTA) and stained for 30 minutes at 4° C. in the dark with a combination of fluorochrome-conjugated antibodies diluted in 50 µl FWB. After staining, the cells were washed once with 2 ml FWB and resuspended in 300 µl FWB for acquisition.

Standard procedures for non-sterile removal of spleen and thymus were followed. Organs were dispersed into single-cell suspensions by forcing the tissue through a 70 µm cell strainer (Falcon, Becton Dickinson Labware, Bedford, Mass.). For FACS analysis, RBCs were lysed by hypotonic lysis, washed, and 1×10$^6$ cells were incubated with 10 μl anti-CD16/CD32 (Fc Block™, BD-PharMingen, San Diego, Calif.) (1/10 dilution in FWB) for 15 minutes at 4° C. The cells were stained with a combination of fluorochrome-conjugated antibodies diluted in 50-100 μl FWB, added directly to the cells in Fc Block, for 30 minutes at 4° C. in the dark. After staining the cells were washed once with 1 ml FWB, and resuspended in 300 μl FWB for acquisition. All antibodies were purchased from BD-PharMingen, San Diego, Calif. unless otherwise specified. Samples were analyzed using a FACSCalibur flow cytometer and CellQuest Pro software (Becton Dickinson Immunocytometry Systems, San Jose, Calif.).

Antibody mixes used for the thymus were: TCRb APC Cy7; CD4 APC; CD8 PerCP; CD69 FITC; and CD62L PE1. Antibody mixes used for spleen and blood were: B220 PerCP; TCRb APC; CD4 APC Cy7; CD8 PE Cy7; CD69 FITC; and CD62L PE.

6.18. Measuring Effects on S1P Levels in Mice

Levels of S1P in mouse (F1 hybrids of 129/B6 strain) spleen were measured using an adaptation of the radio-receptor binding assay described in Murata, N., et al., *Anal. Biochem.* 282:115-120 (2000). This method utilized HEK293F cells overexpressing Edg-1, one of the S1P receptor subtypes, and was based on the competition of labeled S1P with unlabeled S1P in a given sample.

HEK293F cells were transfected with a pEFneo S1P receptor (Edg-1)-expression vector and a G418-resistant cell clone was selected. The Edg-1-expressing HEK293F cells were cultured on 12 multiplates in DMEM containing 5% (v/v) FBS in a humidified air:$CO_2$ (19:1) atmosphere. Twenty four hours before the experiment, the medium was changed to fresh DMEM (without serum) containing 0.1% (w/v) BSA.

Eighteen hours after the test compound was administered, mice were sacrificed and their spleens were removed and frozen. S1P was obtained from the frozen tissue using known methods. See e.g., Yatomi, Y., et al., *FEBS Lett.* 404:173-174 (1997). In particular, 10 mouse spleens in 1 ml ice cold 50 mM phosphate buffer (pH 7.5) containing 1 mM EGTA, 1 mM DTT and Roche complete protease inhibitors were homogenized three times at one minute intervals on ice. The result is centrifuged at 2500 rpm and 4° C. for 10 minutes to remove cell debris. The supernatant was then ultracentrifuged at 45000 rpm and 4° C. in a 70Ti rotor for 1 hour to pull down the membrane-associated proteins. The supernatant was discarded, and the pellet was resuspended in minimal volume (~1 ml) of ice cold 50 mM phosphate buffer (pH 7.5) containing 1 mM EGTA, 1 mM DTT and 33% glycerol with Roche complete protease inhibitors present. The total protein concentration was measured using the Bradford assay.

S1P was extracted into chloroform/KCl/$NH_4OH$ (pH ~12), and the upper aqueous phase is kept. It was then extracted in chloroform/methanol/HCl (pH<1), and the lower organic phase was kept and evaporated to provide S1P, which was stored in a freezer until used. Just before the assay, the dried sample was dissolved by sonication in a binder buffer consisting of 20 mM Tris-HCl (pH 7.5), 100 mM NaCl, 15 mM NaF, and 0.4% (w/v) BSA.

The S1P content of a sample was measured by a radioreceptor-binding assay based on a competitive binding of [$^{33}$P] S1P with S1P in the sample on Edg-1-expressing cells. Edg-1-expressing HEK293F cells in confluent 12 multiplates were washed twice with the ice-cold binding buffer and then incubated with the same buffer containing 1 nM [$^{33}$P]S1P (about 18.00 dpm per well) and increasing doses of authentic S1P or test sample in a final volume of 0.4 ml. The plates were kept on ice for 30 minutes, and the cells were washed twice with the same ice-cold binding buffer to remove unbound ligand. The cells were solubilized with a solution composed of 0.1% SDS, 0.4% NaOH, and 2% $Na_2CO_3$, and the radioactivity was counted by a liquid scintillation counter. The S1P content in the assay well was estimated by extrapolation from the standard displacement curve. The content of S1P in the initial test sample(s) was calculated by multiplying the value obtained from the standard curve by the recovery efficiency of S1P extraction and the dilution factor.

6.19. Rat Adjuvant-Induced Arthritis Model

The effect of a S1P lyase inhibitor ("Compound") in combination with methotrexate ("MTX") was assessed in an adjuvant-induced arthritis (AA) model using Lewis rats. Adjuvant-induced arthritis is a widely used rat model of rheumatoid arthritis (RA), a disease of the joint caused by autoimmune and inflammatory processes. In the majority of published studies, MTX treatment alone is not effective in this model when used in a therapeutic setting, i.e., in an established disease state.

To initiate arthritis, rats were injected intradermally at the base of the tail with 600 μg of *Mycobacterium tuberculosis* in 60 μl of incomplete Freund's adjuvant. Animals were monitored for signs of arthritis by clinical scoring and measuring the volume of the paws using a plethysmometer (model 7140; Ugo Basile North America, Schwenksville, Pa., USA). The values for the two hindpaws were averaged, and the extent of swelling was calculated by subtracting the baseline values of the first measurement from the values of subsequent measurements. Disease severity scores were used to evaluate the severity of the inflammation; a widely used visual scoring of 0 to 4 was used, wherein: 0=normal, no evidence of erythema and swelling; 1=erythema and mild swelling confined to the mid-foot or ankle joint or individual digits; 2=erythema and mild swelling extending to the ankle and the mid-foot or swelling in more than one digit; 3=erythema and moderate swelling extending from the ankle to the metatarsal joints; and 4=erythema and severe swelling encompassing the ankle, foot and digits. Individual scores were recorded as a sum of clinical scores for the two hind paws for each animal. Rats were dosed orally, once a day, with Compound (30 mg/kg), MTX (0.2 mg/kg), a combination of the compounds, or with vehicle (0.1×PBS pH 7.2). Ten rats were used for each treatment group. Compounds were administered after 50% of the animals exhibited disease symptoms, which in this experiment coincided with the day on which half maximal mean paw swelling and clinical score were observed.

As shown in FIG. 1, the combined treatment with Compound and MTX was significantly more effective than treatment with either Compound or MTX alone.

6.20. Transplantation Model

The effect of a S1P lyase inhibitor ("Compound") in combination with cyclosporin A ("CyA") was assessed in a transplantation model, in which tail skin from Balb/C mice was grafted onto the backs of C57Bl/6x129 F1 recipients.

Grafts and graft beds were obtained by removing approximately 1 cm$^2$ of full-thickness skin with a #10 scalpel blade from the ventral tail and back of anesthetized donors and recipients, respectively. Explants from sex-matched donor mice were placed on the prepared graft beds of the recipients and the graft bed was covered with double-thickness Vaseline gauze followed by plaster bandage. Grafts were monitored by visual inspection daily after the removal of the bandage on day 8, and considered rejected when more than 90% was necrotic. Compound was tested alone or in combination with cyclosporin. Each compound (separately) and the combination was dissolved in sterile 95:5 water:ethanol mixture (vehicle). Once daily oral dosing started 3 days prior to transplant and continued daily throughout the experiment.

As shown in FIG. 2A, the administration of cyclosporin alone did not delay graft rejection at a dose of 5 mg/kg, but co-administration with 100 mg/kg of Compound resulted in a significant increase in graft rejection time (from 10.5±0.5 days to 13±0.5 days). FIG. 2B shows the effect of co-administration on the number of mice with greater than 10 days of graft survival.

All references (e.g., patents and patent applications) cited above are incorporated herein by reference in their entireties.

What is claimed is:

1. A method of treating rheumatoid arthritis or graft-versus-host disease, which comprises administering to a patient in need thereof an immunosuppressant and a compound of the formula:

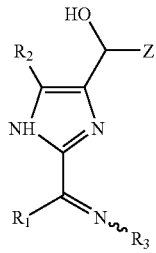

or a pharmaceutically acceptable salt thereof, wherein:
Z is optionally substituted alkyl;
$R_1$ is hydrogen or optionally substituted alkyl or aryl;
$R_2$ is hydrogen or optionally substituted lower alkyl;
$R_3$ is $OR_{3A}$, $NHC(O)R_{3A}$, $NHSO_2R_{3A}$ or hydrogen; and
$R_{3A}$ is independently hydrogen or optionally substituted alkyl, aryl, alkylaryl, arylalkyl, heteroalkyl, heterocycle, alkylheterocycle, or heterocyclealkyl;
and wherein the immunosuppressant is methotrexate or cyclosporin.

2. The method of claim 1, wherein 1, is alkyl optionally substituted with one or more hydroxyl or acetate moieties.

3. The method of claim 1, wherein the compound is of the formula:

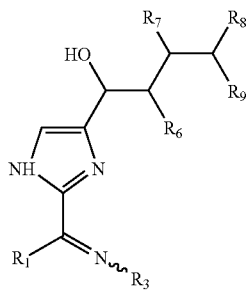

wherein:
$R_6$ is $OR_{6A}$ or $OC(O)R_{6A}$;
$R_7$ is $OR_{7A}$ or $OC(O)R_{7A}$;
$R_8$ is $OR_{8A}$ or $OC(O)R_{8A}$;
$R_9$ is hydrogen, $CH_2OR_{9A}$ or $CH_2OC(O)R_{9A}$; and
each of $R_{6A}$, $R_{7A}$, $R_{8A}$, and $R_{9A}$ is independently hydrogen or lower alkyl.

4. The method of claim 3, wherein the compound is of the formula:

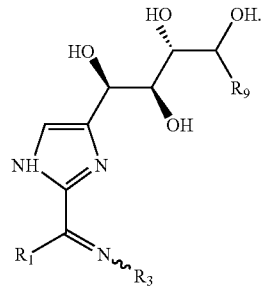

5. The method of claim 4, wherein the compound is of the formula:

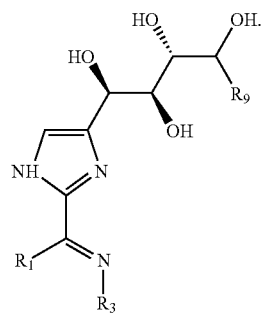

6. The method of claim 4, wherein $R_1$ is lower alkyl.
7. The method of claim 4, wherein $R_3$ is $OR_{3A}$.
8. The method of claim 7, wherein $R_{3A}$ is hydrogen.
9. The method of claim 4, wherein $R_9$ is hydrogen.
10. The method of claim 1, wherein the compound is:
1-(4-((1R,2S,3R)-1,2,3,4-tetrahydroxybutyl)-1H-imidazol-2-yl)-ethanone oxime;
(E)-1-(4-((1R,2S,3R)-1,2,3,4-tetrahydroxybutyl)-1H-imidazol-2-yl)-ethanone oxime;
(Z)-1-(4-((1R,2S,3R)-1,2,3,4-tetrahydroxybutyl)-1H-imidazol-2-yl)-ethanone oxime;
1-(4-((1R,2S,3R)-1,2,3,4-tetrahydroxybutyl)-1H-imidazol-2-yl)ethanone O-methyl oxime;
(E)-1-(4-((1R,2S,3R)-1,2,3,4-tetrahydroxybutyl)-1H-imidazol-2-yl)ethanone O-methyl oxime;
(Z)-1-(4-((1R,2S,3R)-1,2,3,4-tetrahydroxybutyl)-1H-imidazol-2-yl)ethanone O-methyl oxime;
N'-(1-(4-((1R,2S,3R)-1,2,3,4-tetrahydroxybutyl)-1H-imidazol-2-yl)ethylidene)acetohydrazide;
4-methyl-N'-(1-(4-((1R,2S,3R)-1,2,3,4-tetrahydroxybutyl)-1H-imidazol-2-yl)ethylidene)benzenesulfonohydrazide;
(E)-4-methyl-N'-(1-(4-((1R,2S,3R)-1,2,3,4-tetrahydroxybutyl)-1H-imidazol-2-yl)ethylidene)benzenesulfonohydrazide;
(Z)-4-methyl-N'-(1-(4-((1R,2S,3R)-1,2,3,4-tetrahydroxybutyl)-1H-imidazol-2-yl)ethylidene)benzenesulfonohydrazide;

N'-(1-(4-((1R,2S,3R)-1,2,3,4-tetrahydroxybutyl)-1H-imidazol-2-yl)ethylidene)benzohydrazide;

ethyl 2-(1-(4-((1R,2S,3R)-1,2,3,4-tetrahydroxybutyl)-1H-imidazol-2-yl)ethylidene)hydrazinecarboxylate;

(E)-ethyl 2-(1-(4-((1R,2S,3R)-1,2,3,4-tetrahydroxybutyl)-1H-imidazol-2-yl)ethylidene)hydrazinecarboxylate;

(Z)-ethyl 2-(1-(4-((1R,2S,3R)-1,2,3,4-tetrahydroxybutyl)-1H-imidazol-2-yl)ethylidene)hydrazinecarboxylate;

N'-(1-(4-((1R,2S,3R)-1,2,3,4-tetrahydroxybutyl)-1H-imidazol-2-yl)ethylidene)nicotinohydrazide;

(E)-N'-(1-(4-((1R,2S,3R)-1,2,3,4-tetrahydroxybutyl)-1H-imidazol-2-yl)ethylidene)nicotinohydrazide;

(Z)-N'-(1-(4-((1R,2S,3R)-1,2,3,4-tetrahydroxybutyl)-1H-imidazol-2-yl)ethylidene)nicotinohydrazide;

3-chloro-N'-(1-(4-((1R,2S,3R)-1,2,3,4-tetrahydroxybutyl)-1H-imidazol-2-yl)ethylidene)benzohydrazide;

4-fluoro-N'-(1-(4-((1R,2S,3R)-1,2,3,4-tetrahydroxybutyl)-1H-imidazol-2-yl)ethylidene)benzohydrazide;

(E)-4-fluoro-N'-(1-(4-((1R,2S,3R)-1,2,3,4-tetrahydroxybutyl)-1H-imidazol-2-yl)ethylidene)benzohydrazide;

(Z)-4-fluoro-N'-(1-(4-((1R,2S,3R)-1,2,3,4-tetrahydroxybutyl)-1H-imidazol-2-yl)ethylidene)benzohydrazide;

6-amino-N'-(1-(4-((1R,2S,3R)-1,2,3,4-tetrahydroxybutyl)-1H-imidazol-2-yl)ethylidene)nicotinohydrazide;

(E)-6-amino-N'(1-(4-((1R,2S,3R)-1,2,3,4-tetrahydroxybutyl)-1H-imidazol-2-yl)ethylidene)nicotinohydrazide;

(Z)-6-amino-N'-(1-(4-((1R,2S,3R)-1,2,3,4-tetrahydroxybutyl)-1H-imidazol-2-yl)ethylidene)nicotinohydrazide;

N'-(1-(4-((1R,2S,3R)-1,2,3,4-tetrahydroxybutyl)-1H-imidazol-2-yl)ethylidene)isonicotinohydrazide;

(E)-N'-(1-(4-((1R,2S,3R)-1,2,3,4-tetrahydroxybutyl)-1H-imidazol-2-yl)ethylidene)isonicotinohydrazide;

(Z)-N'-(1-(4-((1R,2S,3R)-1,2,3,4-tetrahydroxybutyl)-1H-imidazol-2-yl)ethylidene)isonicotinohydrazide;

N'-(1-(4-((1R,2S,3R)-1,2,3,4-tetrahydroxybutyl)-1H-imidazol-2-yl)ethylidene)biphenyl-3-carbohydrazide;

(E)-N'-(1-(4-((1R,2S,3R)-1,2,3,4-tetrahydroxybutyl)-1H-imidazol-2-yl)ethylidene)biphenyl-3-carbohydrazide;

(Z)-N'-(1-(4-((1R,2S,3R)-1,2,3,4-tetrahydroxybutyl)-1H-imidazol-2-yl)ethylidene)biphenyl-3-carbohydrazide.

11. The method of claim 1, wherein the immunosuppressant is.

12. A method of treating rheumatoid arthritis, which comprises administering to a patient in need thereof therapeutically effective amounts of methotrexate and (E)-1-(4-((1R,2S,3R)-1,2,3,4-tetrahydroxybutyl)-1H-imidazol-2-yl)-ethanone oxime, or a pharmaceutically acceptable salt thereof.

13. A method of treating graft-versus-host disease, which comprises administering to a patient in need thereof therapeutically effective amounts of cyclosporin and (E)-1-(4-((1R,2S,3R)-1,2,3,4-tetrahydroxybutyl)-1H-imidazol-2-yl)-ethanone oxime, or a pharmaceutically acceptable salt thereof.

* * * * *